US006875436B1

(12) United States Patent
Komase et al.

(10) Patent No.: US 6,875,436 B1
(45) Date of Patent: Apr. 5, 2005

(54) **METHOD FOR PRODUCING CELL-FUSHION TYPE *MORBILLIVIRUS* MUTANTS**

(75) Inventors: Katsuhiro Komase, Tokyo (JP); Tetsuo Nakayama, Tokyo (JP); Chikara Aizawa, Kitamoto (JP)

(73) Assignee: The Kitasata Institute, Tokyo (JP)

(*) Notice: Subject to any disclaimer, the term of this patent is extended or adjusted under 35 U.S.C. 154(b) by 0 days.

(21) Appl. No.: 10/149,634

(22) PCT Filed: Oct. 18, 2000

(86) PCT No.: PCT/JP00/07233

§ 371 (c)(1), (2), (4) Date: Oct. 28, 2002

(87) PCT Pub. No.: WO01/38537

PCT Pub. Date: May 31, 2001

(30) Foreign Application Priority Data

Nov. 19, 1999 (JP) .......................................... 11/330099

(51) Int. Cl.$^7$ .................... A61K 39/155; A61K 39/165; A61K 39/175; C12N 7/04; C12N 7/00; C12N 15/45

(52) U.S. Cl. ................................ 424/211.1; 424/212.1; 424/213.1; 435/235.1; 435/236; 435/320.1; 435/471; 435/91.1; 536/23.72

(58) Field of Search .................... 536/23.72; 435/235.1, 435/236, 320.1, 471, 91.1; 424/211.1, 212.1, 213.1

(56) References Cited

U.S. PATENT DOCUMENTS 5,654,136 A * 8/1997 Sasaki et al. .................. 435/5
5,824,777 A * 10/1998 Sasaki et al. ............... 530/350

FOREIGN PATENT DOCUMENTS

EP 864 645 A1 10/1996
WO WO 97/16538 A1 5/1997

OTHER PUBLICATIONS

Makino (Reviews of Infectious Diseases 5:504–505, 1983).*

Buckland, R. et al., "A leucine zipper structure present in the measles virus fusion protein is not required for its tetramerization but is essential for fusion," *Journal of General Virology* (1992) 73:1703–07.

Caballero, M. et al., "Measles virus fusion protein is palmitoylated on transmembrane–intracytoplasmic cysteine residues which participate in cell fusion," *Journal of Virology* (Oct. 1998) 72(10): 8198–204.

Cathomen, T. et al., "Measle viruses with altered envelope protein cytoplasmic tails gain cell fusion competence," *Journal of Virology* (Feb. 1998) 72(2):1224–34.

Evans, S.A. et al., "Nucleotide sequence comparisons of the fusion protein gene from virulent and attenuated strains of rinderpest virus," *Journal of General Virology* (1994) 75:3611–17.

Heider, A. et al., "Comparative investigation of the long non–coding M–F genome region of wild–type and vaccine measles viruses," *Arch. Virol.* (1997) 142: 2521–28.

Hu, A. et al., "Influence of N–linked oligosaccharide chains on the processing, cell surface expression and function of the measles virus fusion protein," *Journal of General Virology* (1995) 76: 705–10.

Maisner, A. et al., "Recombinant measles virus requiring an exogenous protease for activation of infectivity," *Journal of General Virology* (2000) 81:441–49.

Mori, T. et al., "Molecular cloning and complete nucleotide sequence of genomic RNA of the AIK–C strain of attenuated measles virus," *Virus Genes* (1993) 7(1):67–81.

Nakayatama, T. et al., "Fusion–inducing capability of attenutated measles vaccine strain AIK–C," (translation appended), *Extract of 3rd Meeting of the Japanese Society for Vaccinology* (Nov. 20, 1999) pp. 10,72.

Richardson, C.D. et al., "Oligopeptides That Specifically Inhibit Membrane Fusion by Paramyxoviruses: Studies on the Site of Action," *Virology* (1983) 131:518–32.

Takeda, M. et al., "Measles virus attenuation associated with transcriptional impediment and a few amino acid changes in the polymerase and accessory proteins," *Journal of Virology* (Nov. 1998) 72(11): 8690–96.

* cited by examiner

*Primary Examiner*—Mary E. Mosher
(74) *Attorney, Agent, or Firm*—Lahive & Cockfield, LLP; Elizabeth A. Hanley, Esq.

(57) ABSTRACT

It was found that a mutation of an amino acid at a specific position in the F protein of a *morbillivirus* induces a reduction in the cell-fusion ability. By introducing this mutation, a virus having a reduced cell-fusion ability can be produced. Thus, attenuated viruses useful in the preparation of vaccines can be easily produced.

28 Claims, 4 Drawing Sheets

| Construct | Diagram | Fusion |
|---|---|---|
| pAIK-F01 | Bst 1107 at 278¦362; L Y | + |
| pEdm | 237 ... 453 471 494; F  V F ¦ S V S | +++ |
| pMV-F-SVS | L ¦ S V S | + |
| pMV-F-VFY | V F ¦ Y ; Psh AI | +++ |
| pMV-F-VF | V ¦ F | +++ |
| pAIK-F01 | ¦ L Y ; Sal I | + |
| pMV-F278F | F | +++ |
| pMV-F-237V | V  L | + |
| pAIK-F-NULL | L | + |

Figure 4

```
AIK 201 KLGLKLLRYY TEILSLFGPS LRDPISAEIS IQALSYALGG DINKVLEKLG YSGGDLLGIL (SEQ ID NO:10)
Edm 201 KLGLKLLRYY TEILSLFGPS LRDPISAEIS IQALSYALGG DINKVLEKLG YSGGDLLGIL (SEQ ID NO:11)
CDV 313 RLGLRLLRYY TELLSIFGPS LRDPISAEIS IQALIYALGG EIHKILEKLG YSGSDMIAIL (SEQ ID NO:12)
PDV 314 RLGLKLLRYY TELLSIFGPS LRDPISAEIS IQALSYALGG EIHKILEKLG YSGNDMIAIL (SEQ ID NO:13)
RPV 197 KLGLKLLRYY TEILSLFGPS LRDPVSAELS IQALSYALGG DINKILEKLG YSGSDLLAIL (SEQ ID NO:14)

AIK 261 ESRGIKARIT HVDTESYLIV LSIAYPTLSE IKGVIVHRLE GVSYNIGSQE WYTTVPKYVA (SEQ ID NO:5)
Edm 261 ESRGIKARIT HVDTESYFIV LSIAYPTLSE IKGVIVHRLE GVSYNIGSQE WYTTVPKYVA (SEQ ID NO:6)
CDV 373 ESRGIKTKIT HVDLPGKFII LSISYPTLSE VKGVIVHRLE AVSYNIGSQE WYTTVPRYIA (SEQ ID NO:7)
PDV 374 ESRGIKTRIT HVDLPGKFII LSISYPTLSE VKGVIVHRLE AVSYNIGSQE WYTTVPRYVA (SEQ ID NO:8)
RPA 257 ESKGIKAKIT YVDIESYFIV LSIAYPSLSE IKGVIVHRLE SVSYNIGSQE WYTTVPRYVA (SEQ ID NO:9)
```

METHOD FOR PRODUCING CELL-FUSHION TYPE *MORBILLIVIRUS* MUTANTS

TECHNICAL FIELD

The present invention relates to a method for reducing cell-fusion ability by a site-specific mutation of the *morbillivirus*-derived F protein. This F protein is useful in the attenuation of the virus.

BACKGROUND ART

The genus *Morbillivirus* is one of the genera under the family Paramyxoviridae of the order Mononegavirales, including many pathogenic viruses such as the measles virus that causes "measles"—an acute eruptive disorder. The measles virus widely infects infants, expressing symptoms such as fever, eruptions, cough, and such, occasionally causing severe complications such as measles-associated encephalitis, pneumonia, and such, sometimes even death. Furthermore, though very rarely, the measles virus sustains its infection even after the cure of infectious symptoms, causing encephalitis with a poor prognosis, named subacute sclerosing panencephalitis (SSPE). The one and only effective prophylactic means is vaccination with an attenuated measles virus vaccine.

The AIK-C strain, one of the attenuated measles virus vaccines, is a viral strain obtained by continual passage of the measles virus Edmonston strain in sheep kidney cells and chicken embryos cells. The AIK-C strain is excellent in its seroconversion rate as well as safety, which has earned it a high reputation internationally. With the spread of this attenuated measles vaccine, patients who contract measles have noticeably declined in number. In general, the seroconversion rate and safety of a vaccine are two incompatible characteristics, making it difficult to maintain both at a high standard. Therefore, if the mechanism of attenuation used in the AIK-C strain can be applied to other strains and viruses, it will be useful in the development of attenuated vaccines.

However, the mechanism by which this virus strain becomes attenuated remains unclear.

DISCLOSURE OF THE INVENTION

An objective of the present invention is to provide DNA to be used for producing a virus having a reduced cell-fusion ability. Another objective of this invention is to provide a method for reducing the cell-fusion ability of a virus by introducing a site-specific mutation into its F protein, and also to provide a virus having a reduced cell-fusion ability due to a site-specific mutation in its F protein. Viruses having a reduced cell-fusion ability produced by the method of this invention are useful in producing vaccines, and such, as attenuated viruses.

Since cell fusion is profoundly involved in the proliferation and propagation of viruses of the genus *Morbillivirus*, it is assumed that differences in this cell-fusion ability might affect the pathogenicity of the viruses. The present inventors thought that, if a certain mutation in a viral protein is causing a reduction in the cell-fusion ability, it may be possible to control viral proliferation and pathogenicity by identifying that mutation and producing a virus having such a mutant protein.

Therefore, the present inventors expressed the measles virus-derived F and H proteins with mutations introduced at several positions in cells to examine effects of those mutations on the viral cell-fusion ability. As a result, the inventors discovered that the $278^{th}$ amino acid in the F protein is closely associated with the cell-fusion ability. In the Edmonston strain that has a high cell-fusion ability, the $278^{th}$ amino acid in the F protein is phenylalanine. Furthermore, the inventors ascertained that, among F proteins having mutations at several positions, those having phenylalanine at the $278^{th}$ position similar to the Edmonston strain, express a cell-fusion ability equivalent to that of the F protein of the Edmonston strain, and that the cell-fusion ability can be significantly reduced by mutating this amino acid. Thus, this invention is the first to disclose a relationship between the $278^{th}$ amino acid in the F protein and viral cell-fusion ability.

Based on the above-described knowledge, the present inventors discovered that modification of an amino acid at the $278^{th}$ position in the viral F protein enables the reduction of viral cell-fusion ability. Viruses having a reduced cell-fusion ability are thought to become difficult to proliferate and propagate in hosts, which leads to viral attenuation. Isolation of attenuated viruses useful in the development of vaccines has hitherto relied on screening for mutant viral strains, which is a low-efficient and time-consuming procedure. The present invention makes it possible to easily attenuate any desired virus.

Namely, the present invention relates to DNA used in producing viruses having a reduced cell-fusion ability, a method for reducing viral cell-fusion ability by introducing a mutation into a specific amino acid in the viral F protein, and viruses having a reduced cell-fusion ability due to a mutation at a specific position in the F protein, and more specifically relates to each of the following inventions:

[1] a DNA according to (a) or (b), wherein the DNA is used to produce a virus having a reduced cell-fusion ability:
- (a) a DNA encoding a protein derived from the F protein of a virus belonging to the genus *Morbillivirus*, wherein the protein encoded by the DNA comprises an amino acid other than plienylalanine at a position corresponding to the $278^{th}$ position of a protein comprising the amino acid sequence set forth in SEQ ID NO: 2, or
- (b) a DNA encoding a protein having at least a 65% identity to the amino acid sequence set forth in SEQ ID NO: 2, wherein the protein encoded by the DNA comprises an amino acid other than phenylalanine at a position corresponding to the $278^{th}$ position of a protein comprising the amino acid sequence set forth in SEQ ID NO: 2;

[2] the DNA according to [1] that encodes a protein derived from the measles virus;

[3] the DNA according to [1], wherein the amino acid other than phenylalanine is leucine;

[4] a protein encoded by the DNA according to [1];

[5] a vector into which the DNA according to [1] is inserted;

[6] the vector according to [5] used for reconstituting a measles virus with a reduced cell-fusion ability;

[7] a method for reducing the cell-fusion ability of a virus according to (a) or (b), wherein the method comprises the step of introducing a mutation to a position corresponding to the $278^{th}$ amino acid in the protein comprising the amino acid sequence set forth in SEQ ID NO: 2:
- (a) a virus belonging to the genus *Morbillivirus*, or
- (b) a virus comprising a F protein having at least 65% identity to the amino acid sequence set forth in SEQ ID NO: 2;

[8] the method according to [7], wherein the virus is the measles virus;

[9] the method according to [7], comprising substituting the amino acid at a position corresponding to the $278^{th}$ position, with leucine;

[10] a virus with a reduced cell-fusion ability obtained by the method according to [7];

[11] the virus according to [10], wherein the virus is an attenuated virus;

[12] a pharmaceutical composition comprising the virus according to [11]; and,

[13] the pharmaceutical composition according to [12] that is used as a vaccine.

The present invention also relates to the use of DNA in a method for producing a virus having a reduced cell-fusion ability, in which the DNA encodes a protein derived from the F protein of a virus belonging to the genus *Morbillivirus* wherein the protein encoded by the DNA comprises an amino acid other than phenylalanine at a position corresponding to the 278$^{th}$ position of a protein comprising the amino acid sequence set forth in SEQ ID NO: 2. This invention also relates to the use of the DNA in producing a virus with a reduced cell-fusion ability, in which the DNA encodes a protein having at least 65% identity to the amino acid sequence set forth in SEQ ID NO: 2 (Edmonston strain) and has an amino acid other than phenylalanine at a position corresponding to the 278$^{th}$ position of a protein comprising the amino acid sequence set forth in SEQ ID NO: 2 (Edmonston strain). Furthermore, the present invention relates to the use of a vector having such a DNA in reconstituting a measles virus with a reduced cell-fusion ability.

The present invention relates to DNA used for producing a virus having a reduced cell fusion ability. The DNA of this invention include DNA encoding a protein derived from the F protein of virus belonging to the genus *Morbillivirus* and having an amino acid other than phenylalanine at a position corresponding to the 278$^{th}$ position in the F protein of the measles virus Edmonston strain (SEQ ID NO: 2). The DNA of this invention also include DNA encoding a protein having at least 65% identity to the amino acid sequence of the F protein in the Edmonston strain (SEQ ID NO: 2) and having an amino acid other than phenylalanine at a position corresponding to the 278$^{th}$ position in the F protein of the Edmonston strain. Identity to the amino acid sequence set forth in SEQ ID NO: 2 is preferably 80% or more, more preferably 95% or more. Amino acid sequence identity can be determined by the 3 Lipman-Person method using Genetyx-Mac Ver. 10 (Software Development).

Examples of viruses belonging to the genus *Morbillivirus* are the measles virus, canine distemper virus, phocid distemper virus, rinderpest virus, etc.

In this invention, a protein comprising an amino acid sequence having at least 65% identity to the amino acid sequence set forth in SEQ ID NO: 2 has a structure similar to that of a protein comprising the amino acid sequence described in SEQ ID NO: 2. Therefore, it can be assumed that phenylalanine at a position homologous to the 278$^{th}$ position in SEQ ID NO: 2, similarly plays an important role in the maintenance of cell-fusion ability as the phenylalanine at the 278$^{th}$ position in SEQ ID NO: 2. Furthermore, since viruses belonging to the genus *Morbillivirus* are taxonomically closely related to one another, the structure of the F proteins has been conserved among them. Therefore, phenylalanine at a position homologous to the 278$^{th}$ position in SEQ ID NO: 2 can be assumed to play an important role in the maintenance of cell-fusion ability. Results of comparisons of amino acid sequences in the F proteins of viruses belonging to the genus *Morbillivirus* are shown in FIG. 4. Thus, an amino acid corresponding to the 278$^{th}$ position in an amino acid sequence composing the F protein of each virus can be identified.

In this invention, a reduction in the cell-fusion ability of the F protein means a significant reduction in the ability of the F protein compared with an F protein having phenylalanine at a position homologous to the 278$^{th}$ position. More specifically, the significant reduction is exemplified by a reduction of 50%, more preferably 70% or more. Herein, a reduction in the cell-fusion ability includes a complete loss of the ability. Cell-fusion ability of the F protein can be measured by, for example, a computer-assisted image analysis of virus-infected cell sizes under a microscope to calculate the ratio of areas occupied by cells having a predetermined size or more, and comparing these ratios expressed in numerals for each of virus strains. In the case of viruses such as the measles virus capable of growing in floating cells, cell sizes can be analyzed using a flow-cytometer, and such, to numerically express the results for comparison. Cell-fusion ability can be compared also by fixing cells with 0.5% glutaraldehyde, staining them with Giemsa, and observing the size of stained plaques under a microscope.

Cell-fusion ability is considered to be one of the important factors that determine viral proliferation and propagation abilities. Reduction in the cell-fusion ability of a virus is thought to cause a reduction in proliferation and propagation abilities of the virus, resulting in the achievement of viral attenuation. On the other hand, according to this invention, mutation of merely a single amino acid results in attenuation, and therefore, the structure as an antigen is maintained. Therefore, attenuation can be effectively achieved while maintaining the seroconversion rate at a high level.

The amino acid sequence of the F protein in the measles virus Edmonston strain and cDNA sequence encoding the protein are set forth in SEQ ID NOs: 2 and 1, respectively. In a protein of interest, a position homologous to the 278$^{th}$ position in the F protein of the Edmonston strain can be determined by comparing the amino acid sequences. The position in a protein of interest need not be the 278$^{th}$ position. For example, in the case of a protein having the structure of the F protein in the Edmonston strain that has been modified by, for example, an addition, insertion, and/or deletion of one or more amino acids, the homologous position may be a position other than the 278$^{th}$ position. In such a protein, to determine a position homologous to the 278$^{th}$ position in the F protein of the Edmonston strain, amino acid sequences of both proteins are aligned so as to match mutual amino acids as well as amino acids having similar properties as much as possible by inserting appropriate gaps in both amino acid sequences if necessary. Thus, it can be determined which position in a protein of interest corresponds to a position homologous to the 278$^{th}$ position in the F protein of the Edmonston strain. Such a technique has been known among those skilled in the art, and can be performed easily using commercially available or published computer software, for example, the analytical software GENETYX-MAC VER. 10 (Software), etc.

DNA encoding a protein of interest comprising an amino acid other than phenylalanine at a position corresponding to the 278$^{th}$ position in the F protein of the Edmonston strain is used for producing viruses having a reduced cell-fusion ability according to this invention. There is no particular limitation on the origin of these DNA, which may be naturally occurring DNA or DNA into which a mutation has been artificially or spontaneously introduced. Alternatively, they may be DNA comprising artificially designed sequences.

The DNA of the present invention can be prepared using, for example, hybridization techniques well-known in the field (Sambrook, J., Fritsch, E. F., and Maniatis, T. Molecular Cloning: A Laboratory Manual ($2^{nd}$ edition). Cold Spring Harbor Laboratory Press, Cold Spring Harbor). DNA can also be isolated using the polymerase chain reaction technique (Sambrook, J., Fritsch, E. F., and Maniatis, T. Molecular Cloning: A Laboratory Manual ($2^{nd}$ edition). Cold Spring Harbor Laboratory Press, Cold Spring Harbor).

That is, those skilled in the art can isolate DNA by screening virus-derived DNA, and such, using the hybridization technique and PCR method. Nucleotide sequences of probes necessary in the hybridization method and primers required in the PCR method can be designed based on, for example, the cDNA sequence (SEQ ID NO: 1) of the F protein of the Edmonston strain. By identifying the position in the amino acid sequence encoded by the isolated DNA, which is homologous to the $278^{th}$ position in the F protein of the Edmonston strain, a DNA encoding a protein having an amino acid other than phenylalanine at that position can be readily prepared.

By appropriately modifying the DNA thus obtained, the amino acid in the protein encoded by the DNA, which is at a position corresponding to the $278^{th}$ position in the F protein of the Edmonston strain, can be substituted with any desired amino acid other than phenylalanine. Alternatively, the introduction of a mutation so as to delete the phenylalanine is also included in this invention. The amino acid used for the substitution, can be appropriately selected. As described in Examples, a protein having an amino acid that was substituted with leucine at a position homologous to the $278^{th}$ position in the F protein of the Edmonston strain expressed a significant reduction in its the cell-fusion ability. Therefore, DNA encoding a protein having an amino acid that was modified with leucine at a position homologous to the $278^{th}$ position in the F protein of the Edmonston strain can be preferably used in the present invention.

Furthermore, the present invention proved that an amino acid at this position in the F protein has an important function in the cell-fusion ability. Therefore, in the case where an amino acid other than phenylalanine is present at the corresponding position, the cell-fusion ability may be further reduced or, reversely, the degree of the reduction of cell-fusion ability may be lowered by further mutating this amino acid to another amino acid. In this regard, a reduction in the cell-fusion ability includes the loss of the ability as well.

Methods for introducing a mutation into an amino acid in a protein are well known. For example, DNA encoding a desired amino acid sequence can be isolated by preparing a viral library comprising mutant viruses, DNA library encoding mutant F proteins, and such, and screening them for the desired DNA. Alternatively, mutant viruses can be screened from nature. Furthermore, site-specific mutagenesis can be performed using well-known genetic engineering techniques. For the introduction of site-specific mutations, for example, the SOE (splicing-by-overlap-extension)-PCR method (Ho, S. N., Hunt, H. D., Horton, R. M., Pullen, J. K., and Pease, L. R. (1989) Gene 77, 51–59), and Kunkel method (Kunkel, T. A. (1985) Proc. Natl. Acad. Sci. U.S.A. 82 (2): 488–92) can be used.

In addition, in the present invention, as long as the amino acid at a position corresponding to the $278^{th}$ position in the F protein is any amino acid other than phenylalanine, a position other than that may be further modified. For example, the DNA of this invention include DNA encoding proteins having an amino acid other than phenylalanine at the $278^{th}$ position of the F protein in the Edmonston strain (SEQ ID NO: 2) and also having one or more substitution, deletion, insertion, and/or addition of amino acids other than that at the $278^{th}$ position. In the case of the artificial modification of amino acids in the F protein encoded by DNA obtained from viruses belonging to *Morbillivirus*, the number of amino acids modified is usually five or less, preferably three or less, even more preferably, one amino acid excluding the one at the position corresponding to the $278^{th}$ position. Such an amino acid modification can be performed, for example, aiming at further reducing the cell-fusion ability of the F protein, and also aiming at improving the manipulability of DNA, for example, by the insertion of a restriction enzyme site, and such, and also with the aim of modifying a property of the F protein other than its cell-fusion ability. Mutations of amino acids in proteins may occur also in nature.

In general, to minimize the loss of properties of a protein as much as possible, an amino acid used for substitution is thought to be preferably one with a property similar to the substituted amino acid. For example, Ala, Val, Leu, Ile, Pro, Met, Phe, and Trp are all classified into the non-polar amino acid group, and thought to have similar properties. Furthermore, non-charged amino acids are exemplified by Gly, Ser, Thr, Cys, Tyr, Asn, and Gln. Acidic amino acids are exemplified by Asp and Glu, and basic amino acids by Lys, Arg, and His.

Furthermore, the present invention relates to proteins encoded by the DNA of this invention. Viruses with a lowered cell-fusion ability can be produced using the proteins of this invention. A protein of this invention can be expressed by inserting DNA encoding the protein into an appropriate expression vector, and introducing the vector into host cells. In the measles virus, and such, viruses with a reduced cell-fusion ability can be reconstituted from vectors having DNA encoding the proteins of this invention. Several methods for reconstituting the measles virus from cDNA have been reported, namely, the method of Radecke (Radecke, F., Spielhofer, P., Schneider, H., Kaelin, K., Huber, M., Dotsch, C., Christiansen, G. and Billeter, M. A. (1995) EMBO J. 14(23): 5773–84) and the method of Schneider (Schneider, H., Spielhofer, P., Kaelin, K., Dotsch, C., Radecke, F., Sutter, G. and Billeter, M. A. (1997) J. Virol. Methods 64(1): 57–64). According to these methods, a measles virus can be reconstituted from DNA encoding the N, P, M, F, H, and L proteins of the measles virus. Therefore, by using the DNA of this invention as DNA encoding this F protein, a measles virus with a reduced cell-fusion ability can be reconstituted. That is, transcription of DNA encoding the N, P, M, F, H, and Lproteins allows their transcription products to function as genomic RNA of the measles virus, so that measles viral particles can be formed in the presence of the N, P, and L proteins. The virus thus obtained can be further amplified by infecting the virus to appropriate hosts.

More specifically, RNA is extracted from a measles virus strain to synthesize cDNA. Using the known method of introducing a site-specific mutation, cDNA having a mutation (for example, a substitution with leucine) introduced into a position corresponding to the $278^{th}$ amino acid of the F protein of the wild type strain is prepared. From this cDNA, together with other cDNA coding for other measles virus genes, genomic cDNA corresponding to the entire viral genomic RNA is constructed using the restriction enzyme sites, and cloned downstream of the T7 promoter. Host cells infected with the T7 RNA polymerase-expressing vaccinia virus are cotransfected with a plamid having the above-described viral genomic cDNA and other plasmids into which the N, P, and L genes essential for the transcription and replication of the measles virus are cloned downstream of the T7 promoter, and cultured for a few days. From the culture supernatant thereof, a recombinant measles virus with a reduced cell-fusion ability is recovered. This method enables the attenuation of any measles virus strain. Viruses thus produced can be further amplified in appropriate hosts.

Several methods for reconstituting morbilliviruses other than the measles virus are known. For example, the method of Baron, et al. (Baron, M. D., and Barrett, T. (1997) J. Virol. 71(2): 1265–71); the method of Kai, et al. (Kai, C., Miura, R., Shimizu, F., Sato, H., Fujita, K., Hatama, S., Ohashi, K., Kamima, T., and Takahashi, E. Abstracts of the $47^{th}$ General Assembly of the Japanese Society for Virology (1999), p.289: Preparation of recombinant canine distemper virus using the reverse genetic method), and furthermore, Patent WO97/16538 are known.

In addition to the present invention, it is possible to introduce thermosensitivity into a virus by mutating the viral P protein together with the reduction of cell-fusion ability. The present inventors have proved that a thermosensitive characteristic can be introduced into morbilliviruses using a protein having an amino acid other than leucine at a position corresponding to the $139^{th}$ position of the P protein of the measles virus Edmonston strain. Combination of this knowledge with the instant invention enables one to alter the thermosensitive characteristic together with the reduction in the cell-fusion ability, providing extremely safer vaccine preparations.

In addition, the present invention relates to a method for reducing viral cell-fusion ability. The method of this invention is characterized by introducing a mutation to the amino acid at a position homologous to the $278^{th}$ position in the F protein (SEQ ID NO: 2) of the measles virus Edmonston strain, either in the F protein of viruses belonging to the genus *Morbillivirus*, or a protein having at least 65% identity to the amino acid sequence of the F protein in the Edmonston strain. Cell-fusion ability of viruses obtained by the present invention can be compared by, for example, performing a computer-assisted image analysis of sizes of virus-infected cells observed under a microscope, calculating the ratio of areas occupied by cells having a predetermined size or more, and numerically expressing the results for each viral strain. Furthermore, in the case of viruses such as the measles virus capable of growing in floating cells, the cell-fusion ability can be compared by analyzing the cell size using a flow cytometer and such, and numerically expressing the result. The comparison can be also performed by fixing cells with 0.5% glutaraldehyde followed by the Giemsa staining, and observing sizes of the stained plaques under a microscope.

Viruses thus obtained having a reduced cell-fusion ability are less pathogenic because their proliferation and propagation abilities in hosts are reduced. These viruses are extremely useful for producing safe live vaccines. According to the present invention, any virus strain can be attenuated by modifying its F protein using genetic engineering technology. When a virus of this invention is used as a pharmaceutical composition such as a vaccine, besides the use of the virus itself as a drug, it can be formulated by applying a known pharmaceutical procedure. For example, the virus may be administered as a pharmaceutical preparation by appropriately combining with a pharmacologically acceptable carrier or media, more specifically, sterilized water, physiological saline, a plant oil, emulsifier, suspending agent, surfactant, stabilizer, etc. When using the virus as a vaccine, it can be administered suitably in combination with an adjuvant. Administration to patients can be performed by methods known to those skilled in the art, for example, besides the intra-arterial, intravenous, and subcutaneous injections, it can be given intranasally, transbronchially, intramuscularly, or orally. Doses may vary depending on the weight and age of patients as well as the method of administration, purpose of usage, and so on, and may be appropriately selected by one skilled in the art.

In general, in Japan, the vaccine strain of the measles virus is cultured by inoculation to cultured chicken embryos cells prepared from embryonated eggs produced in SPF facilities approved by the Japanese Ministry of Health and Welfare. After the culture, a stabilizer is added to a vaccine solution that has cleared the germ-free test, and purified to obtain an undiluted vaccine concentrate. This vaccine concentrate is stored at –80° C., and at the same time examined for its safety and efficacy. Vaccine concentrates that have cleared the test are pooled as the final bulk, from which vaccine preparations are made. Those that have cleared repeated national tests and private tests are sold as the final preparation.

Furthernore, the viruses of the present invention can be used as vectors for gene therapy.

All the prior art literatures cited herein are incorporated by reference.

BRIEF DESCRIPTION OF THE DRAWINGS

FIG. 4 represents the results of comparing amino acid sequences of viral F proteins belonging to the genus *Morbillivirus*. Positions homologous to the $278^{th}$ position are enclosed in the box (SEQ ID NOs. 5–9). Shown from the top are amino acid sequences of F proteins of the AIK-C strain (SEQ ID NO. 10), Edmonston strain (SEQ ID NO. 11), canine distemper virus (SEQ ID NO.12), phocid distemper virus (SEQ ID NO. 13), and rinderpest virus (SEQ ID NO. 14).

BEST MODE FOR CARRYING OUT THE INVENTION

The present invention will be described in more detail below with reference to examples, but it is not to be construed as being limited thereto.

EXAMPLE 1

Comparative Analysis of Cell-Fusion Ability of F Protein

From the AIK-C strain passaged in Vero cells and its parent Edmonston strain, the F and H coding regions were amplified by PCR respectively, and were inserted downstream of the T7 promoter of the plasmid BSSK (Short, J. M., Fernandez, J. M., Sorge, J. A. and Huse, W. D. (1988) Nucleic Acids Res. 16 (15), 7583–7600) to construct the F protein-expression plasmids pAIK-F01 and pEdm-F as well as H protein-expression plasmids pAIK-H and pEdm-H. The amino acid sequence of the F protein of the Edmonston strain and cDNA sequence encoding the protein are set forth in SEQ ID NOs: 2 and 1, respectively, and the amino acid sequence of the F protein of the AIK-C strain and cDNA sequence encoding the protein are set forth in SEQ ID NOs: 4 and 3, respectively. After the infection of B95a cells with the vaccinia virus expressing the T7 RNA polymerase, the cells were cotransfected with these expression plasmids, and cell fusion abilities were examined.

TABLE 1

| F protein-expression plasmid | H protein-expression plasmid | Cell fusion |
|---|---|---|
| pAIK-F01 | pAIK-H | + |
| PAIK-F01 | pEdm-H | + |
| pEdm-F | pAIK-H | +++ |
| pEdm-F | pEdm-H | +++ |

+:Cell fusion 25% or less
++:Cell fusion 25–50%
+++:Cell fusion 50% or more

As shown in Table 1, as a result of examining various conbinations of plasmids expressing the F protein and H protein, it became obvious that the magnitude of cell-fusion ability is controlled by the F protein.

To further confirm effects of amino acids at the $278^{th}$ position in the F protein on cell-fusion, the experiment was performed with the AIK-C strain using the plasmids pAIK-F01 and pEdm-F. As described above, in the pAIK-F01 thus constructed, the amino acid at the $362^{nd}$ position was replaced with Tyr (Y) compared to the amino acid sequence (SEQ ID NO: 4) deduced from the nucleotide sequence (SEQ ID NO: 3) of the AIK-C strain previously reported by Mori et al. In the pEdm-F constructed from the Edmonston strain, differences in amino acids were detected at six positions compared to pAIK-F01. These two plasmids were recombined using the restriction enzyme Bst1107 to construct pMV-F-SVS and pMV-F-VFY. Both plasmids were further recombined using Bst1107 and PshAI to construct pMV-F-VF. This plasmid and pAIK-F01 were recombined with SalI to construct pMV-F278Phe.

Figure 1:
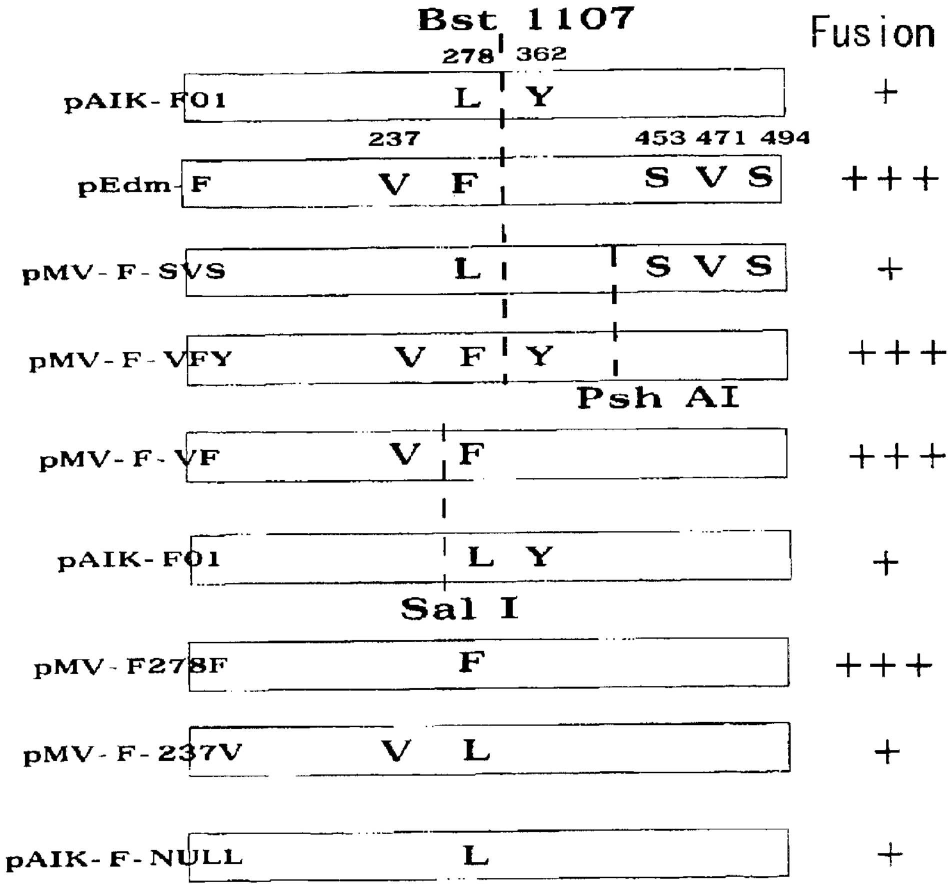
FIG. 1 represents schematic diagrams showing the results of measuring cell-fusion ability F protein mutants. Numerals and alphabets described represent the position of mutations in the amino acid sequences of the F proteins deduced from the nucleotide sequences of pAIK-F01 and pEdm-F, and the amino acids at the positions, respectively. A cell-fusion ability similar to that expressed by the F region plasmid pEdm-F derived from the Edmonston strain is shown with +++.

Using these plasmids and the restriction enzymes SalI, Bst1107, and PshAI, pMV-F-VL was constructed. Using pAIK-H as the H protein expression partner and each of the plasmids, cotransfection was done to determine the cell-fusion ability. As a result, pEdm-F, pMV-F-VFY, pMV-F-VF, pMV-F-278F, which have Phe as the amino acid at the position 278, showed a high cell-fusion ability(FIG. 1). From the aforementioned facts, it became apparent that the low cell-fusion ability of the AIK-C strain is controlled by the amino acid at the $278^{th}$ position in the F protein. That is, the amino acid at the $278^{th}$ position in the F protein of the wild type strain which is Phe (F) results in a high cell-fusion ability. On the other hand, in the AIK-C vaccine strain, this position is mutated to Leu (L), and therefore, this mutation was thought to bring about a reduction in the cell-fusion ability, becoming one of the causes for attenuation.

Figure 2:
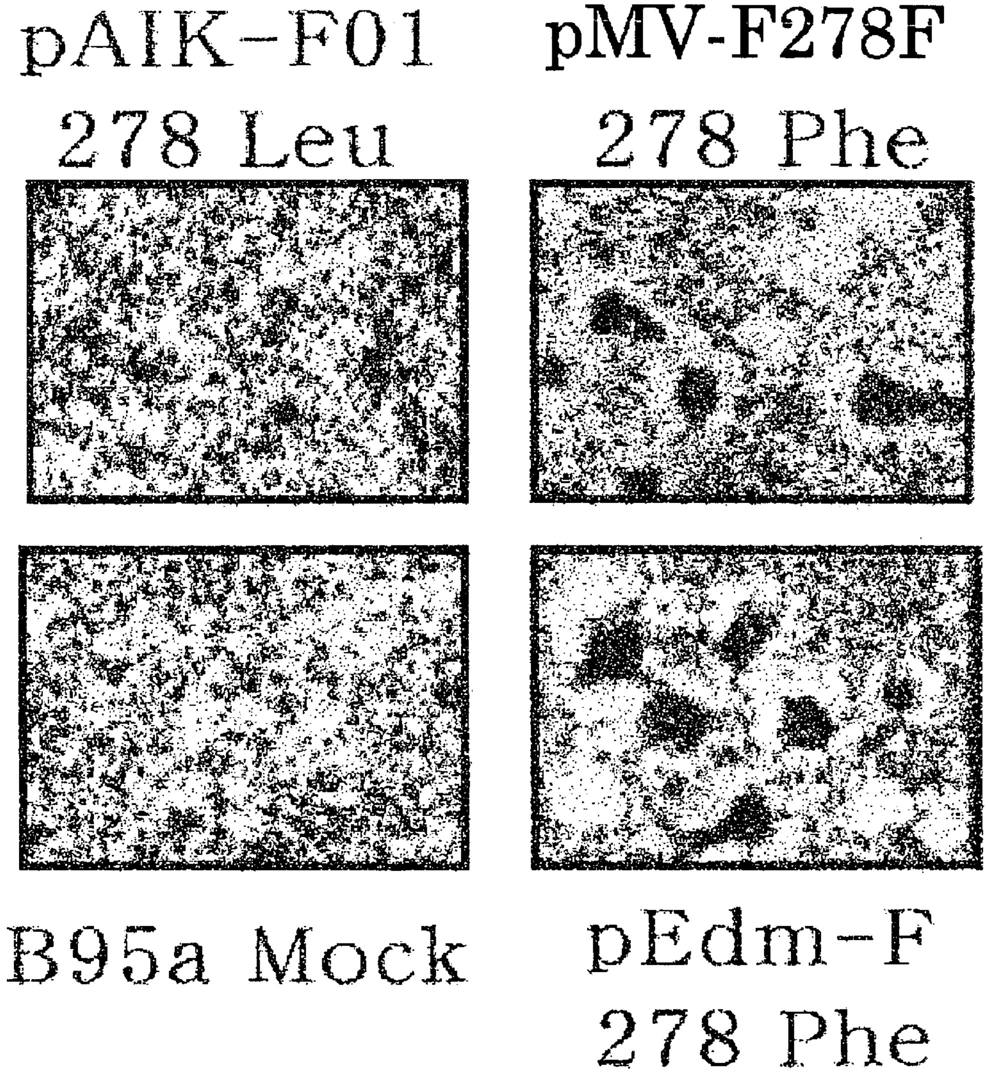
FIG. 2 represents photographs showing the results of cell-fusion observations with F proteins derived from the AIK-C and Edmonston strains, respectively. The photograph marked "278 Leu" shows the result of transformation with a plasmid comprising cDNA encoding a protein having leucine at the $278^{th}$ position thereof. "B95a Mock" shows the result in the case of infection only with the vaccinia virus (vTf7-3).

Cell fusion patterns of cells expressing pAIK-F01 encoding Leu at the $278^{th}$ position, pMV-F278Phe encoding the F protein of the AIK-C strain in which the amino acid at the $278^{th}$ position is mutated to Phe (marked with pMV-F278F in the figure), and pEdm-F encoding the F protein of the Edmonston strain are shown in FIG. 2. When Phe is at the $278^{th}$ position, a formation of remarkable syncytia due to cell-fusion was observed, while, when Leu is at the $278^{th}$ position (marked with pAIK-F01 in the figure), significantly small syncytia were observed.

EXAMPLE 2

Preparation of Measles Virus with Lowered Cell-Fusion Ability

An infectious cDNA clone system was developed based on AIK-C strain and infectious recombinant viruses were recovered from a cDNA genome into which an F protein mutation was introduced. Then, the plaque assay was carried out by using vero cells.

A full-length genome cDNA was constructed based on the measles vaccine AIK-C genome, named MVAK-F278Leu (carrying the F gene of pAIK-F01 in Example 1) in which the amino acid at the $278^{th}$ position in the F protein region is Leu same as that in the AIK-C strain. Then, a full-length genome cDNA named MVAK-F278Phe (carrying the F gene of pMV-F278Phe in Example 1) having the amino acid at the $278^{th}$ position of the F protein replaced with Phe was constructed. These genome cDNAs were cotransfected to B95a cells together with the N-, P-, and L-expression plasmids, and the supernatant was cultured over two generations to recover the infectious recombinant viruses. Viruses thus recovered were infected to Vero cells and cultured at 37° C. for the plaque assay.

Figure 3:
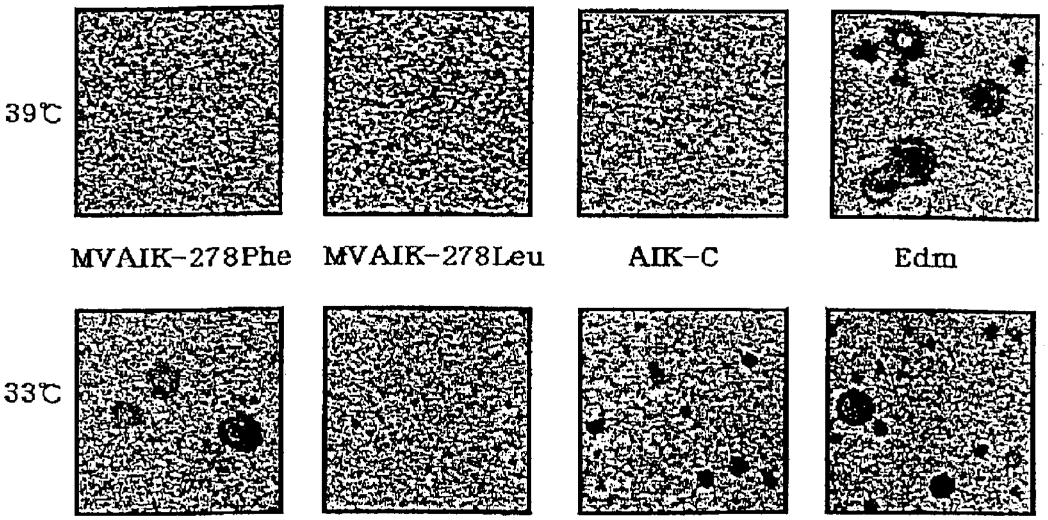
FIG. 3 represents photographs showing the results of plaque assays using Vero cells, in which the infectious viral particles were recovered from a cDNA clone in which a mutation was introduced into the F protein, which was obtained from an infectious clone constructed from the AIK-C strain. Herein, the upper panels show the assay results at the culture temperature 39° C., while the lower panels represent the results at the culture temperature 33° C.
Figure 1:
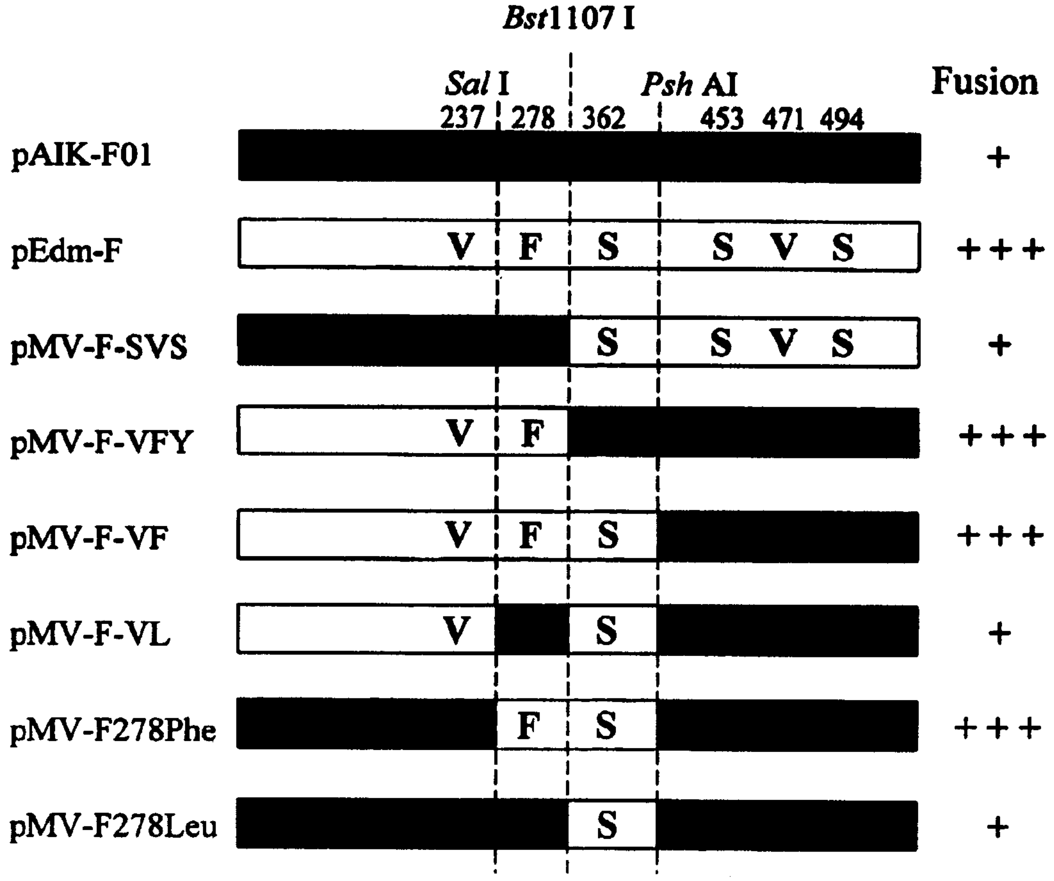
Figure 1:
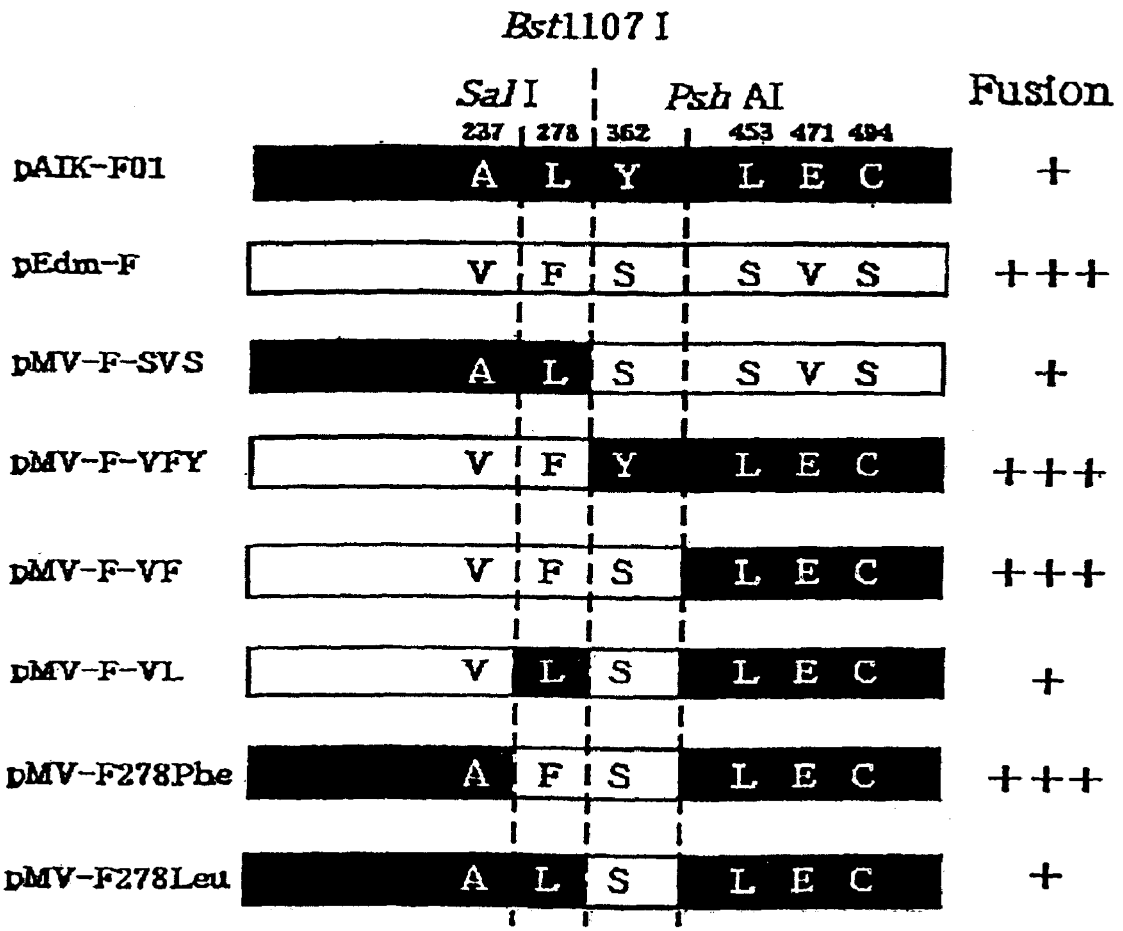

Results are shown in FIG. 3. At 33° C., the recombinant virus into which F278 Phe had been introduced formed large plaques (MVAK-F278Phe), while the virus having the same F278 Leu as the vaccine strain expressed small plaques (MVAK-F278Leu). Most of the plaques formed by the AIK-C vaccine virus at 33° C. were small (AIK-C, 33° C.) with a few large-sized plaques. Furthermore, no plaque was observed with these viruses at 39° C. On the other hand, the parent Edmonston strain expressed large-sized plaques at both 33° C. (Edm, 33° C.) and 39° C. (Edm, 39° C.).

INDUSTRIAL APPLICABILITY

The present invention provides DNA used for producing a virus with a reduced cell-fusion ability, a method for reducing the viral cell-fusion ability by a site-specific mutagenesis of the viral F protein, and viruses with a reduced cell-fusion ability prepared by a site-specific mutation in the F protein. Thus, the instant invention enables the easy production of attenuated viruses, thereby enables the speedy development of live vaccines against novel newly emerging viruses.

Besides the measles virus, the genus *Morbillivirus* in particular includes many pathogenic viruses, such as the canine distemper virus, phocid distemper virus, and rinderpest virus. Therefore, the method of the present invention capable of attenuating viruses of the genus *Morbillivirus* with a minimal mutation is highly useful in the development of vaccines.

What is claimed is:

1. A method for reducing the cell-fusion ability of a virus comprising introducing a mutation in vitro to a position corresponding to the $278^{th}$ amino acid in a protein of the amino acid sequence set forth in SEQ ID NO: 2;

wherein the virus is of the genus *Morbillivirus*; or the virus comprises an F protein having at least 65% identity to the amino acid sequence set forth in SEQ ID NO: 2;

wherein the method does not include converting the virus to a virus identical to measles virus AIK-C.

2. The method according to claim 1, wherein the virus is a measles virus.

3. The method according to claim 1, comprising substituting the amino acid at a position corresponding to the $278^{th}$ position with leucine.

4. The virus with a reduced cell-fusion ability obtained by the method according to claim 1.

5. The virus according to claim 4, wherein the virus is an attenuated virus.

6. A composition comprising the virus according to claim 4, and pharmacologically acceptable carrier or media.

7. The method of claim 1, wherein the virus is a distemper virus or rinderpest virus.

8. The method of claim 1, wherein the protein encoded by the gene is different than the F protein of measles virus AIK-C strain.

9. The method of claim 1, further comprising five or less additional substitutions in the protein.

10. The method of claim 1, further comprising three or less additional substitutions in the protein.

11. The method of claim 1, further comprising one additional substitution in the protein.

12. The method of claim 1, wherein the protein is changed only at the position corresponding to the $278^{th}$ position.

13. The method of claim 1, wherein only the F gene is changed.

14. The method of claim 1, wherein only the F and the P genes are changed.

15. A method of producing a DNA encoding mutant protein having a reduced cell fusion ability, comprising introducing a mutation in vitro so that the mutant protein encoded by the DNA comprises an amino acid other than phenylalanine at the position corresponding to the $278^{th}$ position of a protein of the amino acid sequence of SEQ ID NO: 2; wherein the protein is a protein derived from the F protein of virus belonging to the genus *Morbillivirus*, wherein the protein has phenylalanine at the position corresponding to the $278^{th}$ position of a protein comprising the amino acid sequence of SEQ ID NO: 2; or an F protein having at least 65% identity to the amino acid sequence set forth in SEQ ID NO: 2, wherein the protein has phenylalanine at the position corresponding to the $278^{th}$ position of a protein comprising the amino acid sequence of SEQ ID NO: 2.

16. The method of claim 15, wherein the protein encoded by the DNA is not converted to a protein identical to the F protein of measles virus AIK-C strain.

17. The method of claim 15, further comprising five or less additional substitutions in the protein.

18. The method of claim 15, further comprising three or less additional substitutions in the protein.

19. The method of claim 15, further comprising one additional substitution in the protein.

20. The method of claim 15, wherein the protein is changed only at the position corresponding to the $278^{th}$ position.

21. The method of claim 15, wherein the protein is derived from a measles virus.

22. The method of claim 15, wherein the protein is derived from a distember virus or a rinderpest virus.

23. The method of claim 15, wherein the amino acid at the position corresponding to the $278^{th}$ position is substituted with leucine.

24. An isolated DNA produced by the method of claim 15 or a replicated DNA thereof, wherein the DNA encodes a protein other than the F protein of measles virus AIK-C strain.

25. An isolated protein encoded by the DNA of claim 24.

26. A vector having the DNA of claim 24.

27. The vector of claim 26, wherein the vector encodes a viral genomic RNA.

28. A proliferated virus of the virus according to claim 4, having the mutation at the $278^{th}$ amino acid in the F protein, and with a reduced cell-fusion ability.

* * * * *

UNITED STATES PATENT AND TRADEMARK OFFICE

CERTIFICATE OF CORRECTION

PATENT NO. : 6,875,436 B1 
DATED : April 5, 2005
INVENTOR(S) : Katsuhiro Komase et al.

It is certified that error appears in the above-identified patent and that said Letters Patent is hereby corrected as shown below:

Title page,
Item [54], Title, replace "FUSHION" with -- FUSION --.
Item [75], Inventors, replace "Kitamoto" with -- Saitama --.
Item [73], Assignee, replace "Kitasata" with -- Kitasato --.
Item [56], References Cited, U.S. PATENT DOCUMENTS, "Nakayatama, T. et al.," reference, replace "Nakayatama" with -- Nakayama --.

Column 34,
Line 11, replace "distember" with -- distemper --.

Signed and Sealed this

Twenty-seventh Day of September, 2005

JON W. DUDAS
*Director of the United States Patent and Trademark Office*

UNITED STATES PATENT AND TRADEMARK OFFICE

CERTIFICATE OF CORRECTION

PATENT NO. : 6,875,436 B1 | Page 1 of 2
DATED : April 5, 2005
INVENTOR(S) : Katsuhiro Komase et al.

It is certified that error appears in the above-identified patent and that said Letters Patent is hereby corrected as shown below:

Delete drawing sheet 1, and substitute therefor drawing sheet 1, with the attached sheet.

Signed and Sealed this

Twenty-ninth Day of November, 2005

JON W. DUDAS
*Director of the United States Patent and Trademark Office*

UNITED STATES PATENT AND TRADEMARK OFFICE

CERTIFICATE OF CORRECTION

PATENT NO. : 6,875,436 B1
APPLICATION NO. : 10/149634
DATED : April 5, 2005
INVENTOR(S) : Katsuhiro Komase et al.

It is certified that error appears in the above-identified patent and that said Letters Patent is hereby corrected as shown below:

Delete drawing sheet 1, and substitute therefor drawing sheet 1, with the attached sheet.

This certificate supersedes Certificate of Correction issued November 29, 2005.

Signed and Sealed this

Third Day of October, 2006

JON W. DUDAS
*Director of the United States Patent and Trademark Office*

| | Sal I | Bst1107 I | Psh AI | | | Fusion |
|---|---|---|---|---|---|---|
| | 237 | 278 | 362 | 453 | 471 494 | |
| pAIK-F01 | A | L | Y | L | E C | + |
| pEdm-F | V | F | S | S | V S | +++ |
| pMV-F-SVS | A | L | S | S | V S | + |
| pMV-F-VFY | V | F | Y | L | E C | +++ |
| pMV-F-VF | V | F | S | L | E C | +++ |
| pMV-F-VL | V | L | S | L | E C | + |
| pMV-F278Phe | A | F | S | L | E C | +++ |
| pMV-F278Leu | A | L | S | L | E C | + |

SEQUENCE LISTING

```
<160> NUMBER OF SEQ ID NOS: 14

<210> SEQ ID NO 1
<211> LENGTH: 2373
<212> TYPE: DNA
<213> ORGANISM: Measles virus
<220> FEATURE:
<221> NAME/KEY: CDS
<222> LOCATION: (584)..(2236)

<400> SEQUENCE: 1

agggccaagg aacatacaca cccaacagaa cccagacccc ggcccacggc gccgcgcccc      60

caaccccga caaccagagg gagcccccaa ccaatcccgc cggctccccc ggtgcccaca    120

ggcagggaca ccaaccccg aacagaccca gcacccaacc atcgacaatc caagacgggg    180

gggccccccc aaaaaaaggc ccccaggggc cgacagccag caccgcgagg aagcccaccc    240

accccacaca cgaccacggc aaccaaacca gaacccagac caccctgggc caccagctcc    300

cagactcggc catcaccccg cagaaaggaa aggccacaac ccgcgcaccc cagccccgat    360

ccggcgggga gccacccaac ccgaaccagc acccaagagc gatccccgaa ggaccccga    420

accgcaaagg acatcagtat cccacagcct ctccaagtcc cccggtctcc tcctcttctc    480

gaagggacca aaagatcaat ccaccacacc cgacgacact caactcccca ccccctaaagg    540

agacaccggg aatcccagaa tcaagactca tccaatgtcc atc atg ggt ctc aag      595
                                                Met Gly Leu Lys
                                                  1

gtg aac gtc tct gcc ata ttc atg gca gta ctg tta act ctc caa aca      643
Val Asn Val Ser Ala Ile Phe Met Ala Val Leu Leu Thr Leu Gln Thr
  5                  10                  15                  20

ccc acc ggt caa atc cat tgg ggc aat ctc tct aag ata ggg gtg gta      691
Pro Thr Gly Gln Ile His Trp Gly Asn Leu Ser Lys Ile Gly Val Val
                 25                  30                  35

gga ata gga agt gca agc tac aaa gtt atg act cgt tcc agc cat caa      739
Gly Ile Gly Ser Ala Ser Tyr Lys Val Met Thr Arg Ser Ser His Gln
             40                  45                  50

tca tta gtc ata aaa tta atg ccc aat ata act ctc ctc aat aac tgc      787
Ser Leu Val Ile Lys Leu Met Pro Asn Ile Thr Leu Leu Asn Asn Cys
         55                  60                  65

acg agg gta gag att gca gaa tac agg aga cta ctg aga act gtt ttg      835
Thr Arg Val Glu Ile Ala Glu Tyr Arg Arg Leu Leu Arg Thr Val Leu
     70                  75                  80

gaa cca att aga gat gca ctt aat gca atg acc cag aat ata aga ccg      883
Glu Pro Ile Arg Asp Ala Leu Asn Ala Met Thr Gln Asn Ile Arg Pro
 85                  90                  95                 100

gtt cag agt gta gct tca agt agg aga cac aag aga ttt gcg gga gta      931
Val Gln Ser Val Ala Ser Ser Arg Arg His Lys Arg Phe Ala Gly Val
                105                 110                 115

gtc ctg gca ggt gcg gcc cta ggc gtt gcc aca gct gct cag ata aca      979
Val Leu Ala Gly Ala Ala Leu Gly Val Ala Thr Ala Ala Gln Ile Thr
            120                 125                 130

gcc ggc att gca ctt cac cag tcc atg ctg aac tct caa gcc atc gac     1027
Ala Gly Ile Ala Leu His Gln Ser Met Leu Asn Ser Gln Ala Ile Asp
        135                 140                 145

aat ctg aga gcg agc ctg gaa act act aat cag gca att gag gca atc     1075
Asn Leu Arg Ala Ser Leu Glu Thr Thr Asn Gln Ala Ile Glu Ala Ile
    150                 155                 160
```

-continued

```
aga caa gca ggg cag gag atg ata ttg gct gtt cag ggt gtc caa gac     1123
Arg Gln Ala Gly Gln Glu Met Ile Leu Ala Val Gln Gly Val Gln Asp
165                 170                 175                 180

tac atc aat aat gag ctg ata ccg tct atg aac caa cta tct tgt gat     1171
Tyr Ile Asn Asn Glu Leu Ile Pro Ser Met Asn Gln Leu Ser Cys Asp
                185                 190                 195

tta atc ggc cag aag ctc ggg ctc aaa ttg ctc aga tac tat aca gaa     1219
Leu Ile Gly Gln Lys Leu Gly Leu Lys Leu Leu Arg Tyr Tyr Thr Glu
            200                 205                 210

atc ctg tca tta ttt ggc ccc agc tta cgg gac ccc ata tct gcg gag     1267
Ile Leu Ser Leu Phe Gly Pro Ser Leu Arg Asp Pro Ile Ser Ala Glu
        215                 220                 225

ata tct atc cag gct ttg agc tat gcg ctt gga gga gac atc aat aag     1315
Ile Ser Ile Gln Ala Leu Ser Tyr Ala Leu Gly Gly Asp Ile Asn Lys
    230                 235                 240

gtg tta gaa aag ctc gga tac agt gga ggt gat tta ctg ggc atc tta     1363
Val Leu Glu Lys Leu Gly Tyr Ser Gly Gly Asp Leu Leu Gly Ile Leu
245                 250                 255                 260

gag agc aga gga ata aag gcc cgg ata act cac gtc gac aca gag tcc     1411
Glu Ser Arg Gly Ile Lys Ala Arg Ile Thr His Val Asp Thr Glu Ser
                265                 270                 275

tac ttc att gtc ctc agt ata gcc tat ccg acg ctg tcc gag att aag     1459
Tyr Phe Ile Val Leu Ser Ile Ala Tyr Pro Thr Leu Ser Glu Ile Lys
            280                 285                 290

ggg gtg att gtc cac cgg cta gag ggg gtc tcg tac aac ata ggc tct     1507
Gly Val Ile Val His Arg Leu Glu Gly Val Ser Tyr Asn Ile Gly Ser
        295                 300                 305

caa gag tgg tat acc act gtg ccc aag tat gtc gca acc caa ggg tac     1555
Gln Glu Trp Tyr Thr Thr Val Pro Lys Tyr Val Ala Thr Gln Gly Tyr
    310                 315                 320

ctt atc tcg aat ttt gat gag tca tcg tgt act ttc atg cca gag gga     1603
Leu Ile Ser Asn Phe Asp Glu Ser Ser Cys Thr Phe Met Pro Glu Gly
325                 330                 335                 340

act gtg tgc agc caa aat gcc ttg tac ccg atg agt cct ctg ctc caa     1651
Thr Val Cys Ser Gln Asn Ala Leu Tyr Pro Met Ser Pro Leu Leu Gln
                345                 350                 355

gaa tgc ctc cgg ggg tcc act aag tcc tgt gct cgt aca ctc gta tcc     1699
Glu Cys Leu Arg Gly Ser Thr Lys Ser Cys Ala Arg Thr Leu Val Ser
            360                 365                 370

ggg tct ttt ggg aac cgg ttc att tta tca caa ggg aac cta ata gcc     1747
Gly Ser Phe Gly Asn Arg Phe Ile Leu Ser Gln Gly Asn Leu Ile Ala
        375                 380                 385

aat tgt gca tca atc ctt tgc aag tgt tac aca aca gga acg atc att     1795
Asn Cys Ala Ser Ile Leu Cys Lys Cys Tyr Thr Thr Gly Thr Ile Ile
    390                 395                 400

aat caa gac cct gac aag atc cta aca tac att gct gcc gat cac tgc     1843
Asn Gln Asp Pro Asp Lys Ile Leu Thr Tyr Ile Ala Ala Asp His Cys
405                 410                 415                 420

ccg gta gtc gag gtg aac ggc gtg acc atc caa gtc ggg agc agg agg     1891
Pro Val Val Glu Val Asn Gly Val Thr Ile Gln Val Gly Ser Arg Arg
                425                 430                 435

tat cca gac gct gtg tac ttg cac aga att gac ctc ggt cct ccc ata     1939
Tyr Pro Asp Ala Val Tyr Leu His Arg Ile Asp Leu Gly Pro Pro Ile
            440                 445                 450

tca ttg gag agg ttg gac gta ggg aca aat ctg ggg aat gca att gct     1987
Ser Leu Glu Arg Leu Asp Val Gly Thr Asn Leu Gly Asn Ala Ile Ala
        455                 460                 465

aag ttg gag gat gcc aag gaa ttg ttg gag tca tcg gac cag ata ttg     2035
Lys Leu Glu Asp Ala Lys Glu Leu Leu Glu Ser Ser Asp Gln Ile Leu
    470                 475                 480
```

-continued

```
agg agt atg aaa ggt tta tcg agc act agc ata gtc tac atc ctg att     2083
Arg Ser Met Lys Gly Leu Ser Ser Thr Ser Ile Val Tyr Ile Leu Ile
485                 490                 495                 500

gca gtg tgt ctt gga ggg ttg ata ggg atc ccc gct tta ata tgt tgc     2131
Ala Val Cys Leu Gly Gly Leu Ile Gly Ile Pro Ala Leu Ile Cys Cys
                505                 510                 515

tgc agg ggg cgt tgt aat aaa aag gga gaa caa gtt ggt atg tca aga     2179
Cys Arg Gly Arg Cys Asn Lys Lys Gly Glu Gln Val Gly Met Ser Arg
            520                 525                 530

cca ggc cta aag cct gat ctt acg gga aca tca aaa tcc tat gta agg     2227
Pro Gly Leu Lys Pro Asp Leu Thr Gly Thr Ser Lys Ser Tyr Val Arg
        535                 540                 545

tcg ctc tga tcctctacaa ctcttgaaac acaaatgtcc cacaagtctc             2276
Ser Leu
    550

ctcttcgtca tcaagcaacc accgcaccca gcatcaagcc cacctgaaat tatctccggt   2336

ttccctctgg ccgaacaata tcggtagtta attaaaa                            2373


<210> SEQ ID NO 2
<211> LENGTH: 550
<212> TYPE: PRT
<213> ORGANISM: Measles virus

<400> SEQUENCE: 2

Met Gly Leu Lys Val Asn Val Ser Ala Ile Phe Met Ala Val Leu Leu
  1               5                  10                  15

Thr Leu Gln Thr Pro Thr Gly Gln Ile His Trp Gly Asn Leu Ser Lys
            20                  25                  30

Ile Gly Val Val Gly Ile Gly Ser Ala Ser Tyr Lys Val Met Thr Arg
        35                  40                  45

Ser Ser His Gln Ser Leu Val Ile Lys Leu Met Pro Asn Ile Thr Leu
     50                  55                  60

Leu Asn Asn Cys Thr Arg Val Glu Ile Ala Glu Tyr Arg Arg Leu Leu
 65                  70                  75                  80

Arg Thr Val Leu Glu Pro Ile Arg Asp Ala Leu Asn Ala Met Thr Gln
                 85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
        115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
        195                 200                 205

Tyr Tyr Thr Glu Ile Leu Ser Leu Phe Gly Pro Ser Leu Arg Asp Pro
    210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255
```

-continued

```
Leu Gly Ile Leu Glu Ser Arg Gly Ile Lys Ala Arg Ile Thr His Val
            260                 265                 270

Asp Thr Glu Ser Tyr Phe Ile Val Leu Ser Ile Ala Tyr Pro Thr Leu
        275                 280                 285

Ser Glu Ile Lys Gly Val Ile Val His Arg Leu Glu Gly Val Ser Tyr
    290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
        355                 360                 365

Thr Leu Val Ser Gly Ser Phe Gly Asn Arg Phe Ile Leu Ser Gln Gly
    370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
        435                 440                 445

Gly Pro Pro Ile Ser Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Ser Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550
```

<210> SEQ ID NO 3
<211> LENGTH: 2372
<212> TYPE: DNA
<213> ORGANISM: Measles virus
<220> FEATURE:
<221> NAME/KEY: CDS
<222> LOCATION: (583)..(2235)

<400> SEQUENCE: 3

```
agggccaagg aacatacaca cccaacagaa cccagacccc ggcccacggc gccgcgcccc      60

caaccccga caaccagagg gagcccccaa ccaatcccgc cggctccccc ggtgcccaca     120

ggcagggaca ccaaccccg aacagaccca gcacccaacc atcgacaatc caagacgggg     180

gggccccccc aaaaaaaggc ccccagggc cgacagccag caccgcgagg aagcccaccc     240

accccacaca cgaccacggc aaccaaacca gaacccagac caccctggcc accagctccc    300

agactcggcc atcaccccgc agaaaggaaa ggccacaacc cgcgcacccc agccccgatc    360
```

-continued

```
cggcggggag ccacccaacc cgaaccagca cccaagagcg atccccgaag gacccccgaa    420

ccgcaaagga catcagtatc ccacagcctc tccaagtccc ccggtctcct cctcttctcg    480

aagggaccaa aagatcaatc caccacaccc gacgacactc aactccccac ccctaaagga    540

gacaccggga atcccagaat caagactcat ccaatgtcca tc atg ggt ctc aag      594
                                                Met Gly Leu Lys
                                                  1

gtg aac gtc tct gcc ata ttc atg gca gta ctg tta act ctc caa aca      642
Val Asn Val Ser Ala Ile Phe Met Ala Val Leu Leu Thr Leu Gln Thr
  5                  10                  15                  20

ccc acc ggt caa atc cat tgg ggc aat ctc tct aag ata ggg gtg gta      690
Pro Thr Gly Gln Ile His Trp Gly Asn Leu Ser Lys Ile Gly Val Val
                 25                  30                  35

gga ata gga agt gca agc tac aaa gtt atg act cgt tcc agc cat caa      738
Gly Ile Gly Ser Ala Ser Tyr Lys Val Met Thr Arg Ser Ser His Gln
             40                  45                  50

tca tta gtc ata aaa tta atg ccc aat ata act ctc ctc aat aac tgc      786
Ser Leu Val Ile Lys Leu Met Pro Asn Ile Thr Leu Leu Asn Asn Cys
         55                  60                  65

acg agg gta gag att gca gaa tac agg aga cta ctg aga aca gtt ttg      834
Thr Arg Val Glu Ile Ala Glu Tyr Arg Arg Leu Leu Arg Thr Val Leu
     70                  75                  80

gaa cca att aga gat gca ctt aat gca atg acc cag aat ata aga ccg      882
Glu Pro Ile Arg Asp Ala Leu Asn Ala Met Thr Gln Asn Ile Arg Pro
 85                  90                  95                 100

gtt cag agt gta gct tca agt agg aga cac aag aga ttt gcg gga gta      930
Val Gln Ser Val Ala Ser Ser Arg Arg His Lys Arg Phe Ala Gly Val
                105                 110                 115

gtc ctg gca ggt gcg gcc cta ggc gtt gcc aca gct gct cag ata aca      978
Val Leu Ala Gly Ala Ala Leu Gly Val Ala Thr Ala Ala Gln Ile Thr
            120                 125                 130

gcc ggc att gca ctt cac cag tcc atg ctg aac tct caa gcc atc gac     1026
Ala Gly Ile Ala Leu His Gln Ser Met Leu Asn Ser Gln Ala Ile Asp
        135                 140                 145

aat ctg aga gcg agc ctg gaa act act aat cag gca att gag gca atc     1074
Asn Leu Arg Ala Ser Leu Glu Thr Thr Asn Gln Ala Ile Glu Ala Ile
    150                 155                 160

aga caa gca ggg cag gag atg ata ttg gct gtt cag ggt gtc caa gac     1122
Arg Gln Ala Gly Gln Glu Met Ile Leu Ala Val Gln Gly Val Gln Asp
165                 170                 175                 180

tac atc aat aat gag ctg ata ccg tct atg aac caa cta tct tgt gat     1170
Tyr Ile Asn Asn Glu Leu Ile Pro Ser Met Asn Gln Leu Ser Cys Asp
                185                 190                 195

tta atc ggc cag aag ctc ggg ctc aaa ttg ctc aga tac tat aca gaa     1218
Leu Ile Gly Gln Lys Leu Gly Leu Lys Leu Leu Arg Tyr Tyr Thr Glu
            200                 205                 210

atc ctg tca tta ttt ggc ccc agc tta cgg gac ccc ata tct gcg gag     1266
Ile Leu Ser Leu Phe Gly Pro Ser Leu Arg Asp Pro Ile Ser Ala Glu
        215                 220                 225

ata tct atc cag gct ttg agc tat gcg ctt gga gga gac atc aat aag     1314
Ile Ser Ile Gln Ala Leu Ser Tyr Ala Leu Gly Gly Asp Ile Asn Lys
    230                 235                 240

gtg tta gaa aag ctc gga tac agt gga ggt gat tta ctg ggc atc tta     1362
Val Leu Glu Lys Leu Gly Tyr Ser Gly Gly Asp Leu Leu Gly Ile Leu
245                 250                 255                 260

gag agc aga gga ata aag gcc cgg ata act cac gtc gac aca gag tcc     1410
Glu Ser Arg Gly Ile Lys Ala Arg Ile Thr His Val Asp Thr Glu Ser
                265                 270                 275
```

-continued

```
tac tta att gtc ctc agt ata gcc tat ccg acg ctg tcc gag att aag      1458
Tyr Leu Ile Val Leu Ser Ile Ala Tyr Pro Thr Leu Ser Glu Ile Lys
            280                 285                 290

ggg gtg att gtc cac cgg cta gag ggg gtc tcg tac aac ata ggc tct      1506
Gly Val Ile Val His Arg Leu Glu Gly Val Ser Tyr Asn Ile Gly Ser
        295                 300                 305

caa gag tgg tat acc act gtg ccc aag tat gtt gca acc caa ggg tac      1554
Gln Glu Trp Tyr Thr Thr Val Pro Lys Tyr Val Ala Thr Gln Gly Tyr
    310                 315                 320

ctt atc tcg aat ttt gat gag tca tcg tgt act ttc atg cca gag ggg      1602
Leu Ile Ser Asn Phe Asp Glu Ser Ser Cys Thr Phe Met Pro Glu Gly
325                 330                 335                 340

act gtg tgc agc caa aat gcc ttg tac ccg atg agt cct ctg ctc caa      1650
Thr Val Cys Ser Gln Asn Ala Leu Tyr Pro Met Ser Pro Leu Leu Gln
                345                 350                 355

gaa tgc ctc cgg ggg tcc acc aag tcc tgt gct cgt aca ctc gta tcc      1698
Glu Cys Leu Arg Gly Ser Thr Lys Ser Cys Ala Arg Thr Leu Val Ser
            360                 365                 370
ggg tct ttt ggg aac cgg ttc att tta tca caa ggg aac cta ata gcc      1746
Gly Ser Phe Gly Asn Arg Phe Ile Leu Ser Gln Gly Asn Leu Ile Ala
        375                 380                 385

aat tgt gca tca atc ctt tgc aag tgt tac aca aca gga acg atc att      1794
Asn Cys Ala Ser Ile Leu Cys Lys Cys Tyr Thr Thr Gly Thr Ile Ile
    390                 395                 400

aat caa gac cct gac aag atc cta aca tac att gct gcc gat cac tgc      1842
Asn Gln Asp Pro Asp Lys Ile Leu Thr Tyr Ile Ala Ala Asp His Cys
405                 410                 415                 420

ccg gta gtc gag gtg aac ggc gtg acc atc caa gtc ggg agc agg agg      1890
Pro Val Val Glu Val Asn Gly Val Thr Ile Gln Val Gly Ser Arg Arg
                425                 430                 435

tat cca gac gct gtg tac ttg cac aga att gac ctc ggt cct ccc ata      1938
Tyr Pro Asp Ala Val Tyr Leu His Arg Ile Asp Leu Gly Pro Pro Ile
            440                 445                 450

tta ttg gag agg ttg gac gta ggg aca aat ctg ggg aat gca att gct      1986
Leu Leu Glu Arg Leu Asp Val Gly Thr Asn Leu Gly Asn Ala Ile Ala
        455                 460                 465

aag ttg gag gat gcc aag gaa ttg ttg gag tca tcg gac cag ata ttg      2034
Lys Leu Glu Asp Ala Lys Glu Leu Leu Glu Ser Ser Asp Gln Ile Leu
    470                 475                 480

agg agt atg aaa ggt tta tcg agc act tgc ata gtc tac atc ctg att      2082
Arg Ser Met Lys Gly Leu Ser Ser Thr Cys Ile Val Tyr Ile Leu Ile
485                 490                 495                 500

gca gtg tgt ctt gga ggg ttg ata ggg atc ccc gct tta ata tgt tgc      2130
Ala Val Cys Leu Gly Gly Leu Ile Gly Ile Pro Ala Leu Ile Cys Cys
                505                 510                 515

tgc agg ggg cgt tgt aac aaa aag gga gaa caa gtt ggt atg tca aga      2178
Cys Arg Gly Arg Cys Asn Lys Lys Gly Glu Gln Val Gly Met Ser Arg
            520                 525                 530

cca ggc cta aag cct gat ctt acg gga aca tca aaa tcc tat gta agg      2226
Pro Gly Leu Lys Pro Asp Leu Thr Gly Thr Ser Lys Ser Tyr Val Arg
        535                 540                 545

tcg ctc tga tcctctacaa ctcttgaaac acaaatgtcc cacaagtctc             2275
Ser Leu
    550

ctcttcgtca tcaagcaacc accgcaccca gcatcaagcc cacctgaaat tatctccggc   2335

ttccctctgg ccgaacaata tcggtagtta attaaaa                            2372
```

-continued

<210> SEQ ID NO 4
<211> LENGTH: 550
<212> TYPE: PRT
<213> ORGANISM: Measles virus

<400> SEQUENCE: 4

```
Met Gly Leu Lys Val Asn Val Ser Ala Ile Phe Met Ala Val Leu Leu
  1               5                  10                  15

Thr Leu Gln Thr Pro Thr Gly Gln Ile His Trp Gly Asn Leu Ser Lys
             20                  25                  30

Ile Gly Val Val Gly Ile Gly Ser Ala Ser Tyr Lys Val Met Thr Arg
         35                  40                  45

Ser Ser His Gln Ser Leu Val Ile Lys Leu Met Pro Asn Ile Thr Leu
     50                  55                  60

Leu Asn Asn Cys Thr Arg Val Glu Ile Ala Glu Tyr Arg Arg Leu Leu
 65                  70                  75                  80

Arg Thr Val Leu Glu Pro Ile Arg Asp Ala Leu Asn Ala Met Thr Gln
                 85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
        115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Ala Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
        195                 200                 205

Tyr Tyr Thr Glu Ile Leu Ser Leu Phe Gly Pro Ser Leu Arg Asp Pro
    210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Arg Gly Ile Lys Ala Arg Ile Thr His Val
            260                 265                 270

Asp Thr Glu Ser Tyr Leu Ile Val Leu Ser Ile Ala Tyr Pro Thr Leu
        275                 280                 285

Ser Glu Ile Lys Gly Val Ile Val His Arg Leu Glu Gly Val Ser Tyr
    290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Ser Thr Lys Ser Cys Ala Arg
        355                 360                 365

Thr Leu Val Ser Gly Ser Phe Gly Asn Arg Phe Ile Leu Ser Gln Gly
    370                 375                 380
```

-continued

```
Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

Ala Asp His Cys Pro Val Val Glu Val Asn Gly Val Thr Ile Gln Val
            420                 425                 430

Gly Ser Arg Arg Tyr Pro Asp Ala Val Tyr Leu His Arg Ile Asp Leu
        435                 440                 445

Gly Pro Pro Ile Leu Leu Glu Arg Leu Asp Val Gly Thr Asn Leu Gly
    450                 455                 460

Asn Ala Ile Ala Lys Leu Glu Asp Ala Lys Glu Leu Leu Glu Ser Ser
465                 470                 475                 480

Asp Gln Ile Leu Arg Ser Met Lys Gly Leu Ser Ser Thr Cys Ile Val
                485                 490                 495

Tyr Ile Leu Ile Ala Val Cys Leu Gly Gly Leu Ile Gly Ile Pro Ala
            500                 505                 510

Leu Ile Cys Cys Cys Arg Gly Arg Cys Asn Lys Lys Gly Glu Gln Val
        515                 520                 525

Gly Met Ser Arg Pro Gly Leu Lys Pro Asp Leu Thr Gly Thr Ser Lys
    530                 535                 540

Ser Tyr Val Arg Ser Leu
545                 550


<210> SEQ ID NO 5
<211> LENGTH: 120
<212> TYPE: PRT
<213> ORGANISM: Measles virus

<400> SEQUENCE: 5

Lys Leu Gly Leu Lys Leu Leu Arg Tyr Tyr Thr Glu Ile Leu Ser Leu
1               5                   10                  15

Phe Gly Pro Ser Leu Arg Asp Pro Ile Ser Ala Glu Ile Ser Ile Gln
            20                  25                  30

Ala Leu Ser Tyr Ala Leu Gly Gly Asp Ile Asn Lys Val Leu Glu Lys
        35                  40                  45

Leu Gly Tyr Ser Gly Gly Asp Leu Leu Gly Ile Leu Glu Ser Arg Gly
    50                  55                  60

Ile Lys Ala Arg Ile Thr His Val Asp Thr Glu Ser Tyr Leu Ile Val
65                  70                  75                  80

Leu Ser Ile Ala Tyr Pro Thr Leu Ser Glu Ile Lys Gly Val Ile Val
                85                  90                  95

His Arg Leu Glu Gly Val Ser Tyr Asn Ile Gly Ser Gln Glu Trp Tyr
            100                 105                 110

Thr Thr Val Pro Lys Tyr Val Ala
        115                 120


<210> SEQ ID NO 6
<211> LENGTH: 120
<212> TYPE: PRT
<213> ORGANISM: Measles virus

<400> SEQUENCE: 6

Lys Leu Gly Leu Lys Leu Leu Arg Tyr Tyr Thr Glu Ile Leu Ser Leu
1               5                   10                  15

Phe Gly Pro Ser Leu Arg Asp Pro Ile Ser Ala Glu Ile Ser Ile Gln
            20                  25                  30
```

-continued

```
Ala Leu Ser Tyr Ala Leu Gly Gly Asp Ile Asn Lys Val Leu Glu Lys
        35                  40                  45

Leu Gly Tyr Ser Gly Gly Asp Leu Leu Gly Ile Leu Glu Ser Arg Gly
    50                  55                  60

Ile Lys Ala Arg Ile Thr His Val Asp Thr Glu Ser Tyr Phe Ile Val
65                  70                  75                  80

Leu Ser Ile Ala Tyr Pro Thr Leu Ser Glu Ile Lys Gly Val Ile Val
                85                  90                  95

His Arg Leu Glu Gly Val Ser Tyr Asn Ile Gly Ser Gln Glu Trp Tyr
            100                 105                 110

Thr Thr Val Pro Lys Tyr Val Ala
        115                 120


<210> SEQ ID NO 7
<211> LENGTH: 120
<212> TYPE: PRT
<213> ORGANISM: canine distemper virus

<400> SEQUENCE: 7

Arg Leu Gly Leu Arg Leu Leu Arg Tyr Tyr Thr Glu Leu Leu Ser Ile
1               5                   10                  15

Phe Gly Pro Ser Leu Arg Asp Pro Ile Ser Ala Glu Ile Ser Ile Gln
            20                  25                  30

Ala Leu Ile Tyr Ala Leu Gly Gly Glu Ile His Lys Ile Leu Glu Lys
        35                  40                  45

Leu Gly Tyr Ser Gly Ser Asp Met Ile Ala Ile Leu Glu Ser Arg Gly
    50                  55                  60

Ile Lys Thr Lys Ile Thr His Val Asp Leu Pro Gly Lys Phe Ile Ile
65                  70                  75                  80

Leu Ser Ile Ser Tyr Pro Thr Leu Ser Glu Val Lys Gly Val Ile Val
                85                  90                  95

His Arg Leu Glu Ala Val Ser Tyr Asn Ile Gly Ser Gln Glu Trp Tyr
            100                 105                 110

Thr Thr Val Pro Arg Tyr Ile Ala
        115                 120


<210> SEQ ID NO 8
<211> LENGTH: 120
<212> TYPE: PRT
<213> ORGANISM: phocid distemper virus

<400> SEQUENCE: 8

Arg Leu Gly Leu Lys Leu Leu Arg Tyr Tyr Thr Glu Leu Leu Ser Ile
1               5                   10                  15

Phe Gly Pro Ser Leu Arg Asp Pro Ile Ser Ala Glu Ile Ser Ile Gln
            20                  25                  30

Ala Leu Ser Tyr Ala Leu Gly Gly Glu Ile His Lys Ile Leu Glu Lys
        35                  40                  45

Leu Gly Tyr Ser Gly Asn Asp Met Ile Ala Ile Leu Glu Ser Arg Gly
    50                  55                  60

Ile Lys Thr Arg Ile Thr His Val Asp Leu Pro Gly Lys Phe Ile Ile
65                  70                  75                  80

Leu Ser Ile Ser Tyr Pro Thr Leu Ser Glu Val Lys Gly Val Ile Val
                85                  90                  95
```

-continued

```
His Arg Leu Glu Ala Val Ser Tyr Asn Ile Gly Ser Gln Glu Trp Tyr
            100                 105                 110

Thr Thr Val Pro Arg Tyr Val Ala
        115                 120


<210> SEQ ID NO 9
<211> LENGTH: 120
<212> TYPE: PRT
<213> ORGANISM: Rinderpest virus

<400> SEQUENCE: 9

Lys Leu Gly Leu Lys Leu Leu Arg Tyr Tyr Thr Glu Ile Leu Ser Leu
1               5                   10                  15

Phe Gly Pro Ser Leu Arg Asp Pro Val Ser Ala Glu Leu Ser Ile Gln
            20                  25                  30

Ala Leu Ser Tyr Ala Leu Gly Gly Asp Ile Asn Lys Ile Leu Glu Lys
        35                  40                  45

Leu Gly Tyr Ser Gly Ser Asp Leu Leu Ala Ile Leu Glu Ser Lys Gly
    50                  55                  60

Ile Lys Ala Lys Ile Thr Tyr Val Asp Ile Glu Ser Tyr Phe Ile Val
65                  70                  75                  80

Leu Ser Ile Ala Tyr Pro Ser Leu Ser Glu Ile Lys Gly Val Ile Val
                85                  90                  95

His Arg Leu Glu Ser Val Ser Tyr Asn Ile Gly Ser Gln Glu Trp Tyr
            100                 105                 110

Thr Thr Val Pro Arg Tyr Val Ala
        115                 120


<210> SEQ ID NO 10
<211> LENGTH: 60
<212> TYPE: PRT
<213> ORGANISM: Viral

<400> SEQUENCE: 10

Lys Leu Gly Leu Lys Leu Leu Arg Tyr Tyr Thr Glu Ile Leu Ser Leu
 1               5                  10                  15

Phe Gly Pro Ser Leu Arg Asp Pro Ile Ser Ala Glu Ile Ser Ile Gln
            20                  25                  30

Ala Leu Ser Tyr Ala Leu Gly Gly Asp Ile Asn Lys Val Leu Glu Lys
        35                  40                  45

Leu Gly Tyr Ser Gly Gly Asp Leu Leu Gly Ile Leu
    50                  55                  60


<210> SEQ ID NO 11
<211> LENGTH: 60
<212> TYPE: PRT
<213> ORGANISM: Viral

<400> SEQUENCE: 11

Lys Leu Gly Leu Lys Leu Leu Arg Tyr Tyr Thr Glu Ile Leu Ser Leu
 1               5                  10                  15

Phe Gly Pro Ser Leu Arg Asp Pro Ile Ser Ala Glu Ile Ser Ile Gln
            20                  25                  30

Ala Leu Ser Tyr Ala Leu Gly Gly Asp Ile Asn Lys Val Leu Glu Lys
        35                  40                  45

Leu Gly Tyr Ser Gly Gly Asp Leu Leu Gly Ile Leu
    50                  55                  60
```

-continued

```
<210> SEQ ID NO 12
<211> LENGTH: 60
<212> TYPE: PRT
<213> ORGANISM: Viral

<400> SEQUENCE: 12

Arg Leu Gly Leu Arg Leu Leu Arg Tyr Tyr Thr Glu Leu Leu Ser Ile
 1               5                  10                  15

Phe Gly Pro Ser Leu Arg Asp Pro Ile Ser Ala Glu Ile Ser Ile Gln
            20                  25                  30

Ala Leu Ile Tyr Ala Leu Gly Gly Glu Ile His Lys Ile Leu Glu Lys
        35                  40                  45

Leu Gly Tyr Ser Gly Ser Asp Met Ile Ala Ile Leu
    50                  55                  60


<210> SEQ ID NO 13
<211> LENGTH: 60
<212> TYPE: PRT
<213> ORGANISM: Viral

<400> SEQUENCE: 13

Arg Leu Gly Leu Lys Leu Leu Arg Tyr Tyr Thr Glu Leu Leu Ser Ile
 1               5                  10                  15

Phe Gly Pro Ser Leu Arg Asp Pro Ile Ser Ala Glu Ile Ser Ile Gln
            20                  25                  30

Ala Leu Ser Tyr Ala Leu Gly Gly Glu Ile His Lys Ile Leu Glu Lys
        35                  40                  45

Leu Gly Tyr Ser Gly Asn Asp Met Ile Ala Ile Leu
    50                  55                  60


<210> SEQ ID NO 14
<211> LENGTH: 60
<212> TYPE: PRT
<213> ORGANISM: Viral

<400> SEQUENCE: 14

Lys Leu Gly Leu Lys Leu Leu Arg Tyr Tyr Thr Glu Ile Leu Ser Leu
 1               5                  10                  15

Phe Gly Pro Ser Leu Arg Asp Pro Val Ser Ala Glu Leu Ser Ile Gln
            20                  25                  30

Ala Leu Ser Tyr Ala Leu Gly Gly Asp Ile Asn Lys Ile Leu Glu Lys
        35                  40                  45

Leu Gly Tyr Ser Gly Ser Asp Leu Leu Ala Ile Leu
    50                  55                  60
```